US00PP19155P2

(12) United States Plant Patent
Fischer-Tohl

(10) Patent No.: US PP19,155 P2
(45) Date of Patent: Aug. 26, 2008

(54) ***GERANIUM* PLANT NAMED 'SIL QUIRIN'**

(50) Latin Name: *Pelargonium peltatum*
Varietal Denomination: Sil Quirin

(75) Inventor: Ilse Fischer-Tohl, Kirschlintein (DE)

(73) Assignee: Silze GmbH & Company KG, Weener (DE)

( * ) Notice: Subject to any disclaimer, the term of this patent is extended or adjusted under 35 U.S.C. 154(b) by 0 days.

(21) Appl. No.: 11/974,693

(22) Filed: Oct. 16, 2007

Related U.S. Application Data

(60) Provisional application No. 60/900,012, filed on Feb. 7, 2007.

(51) Int. Cl.
*A01H 5/00* (2006.01)

(52) U.S. Cl. ..... Plt./332

(58) Field of Classification Search ..... Plt./332
See application file for complete search history.

(56) References Cited

PUBLICATIONS

UPOV–ROM search for PBR PEL 02049 for culrivar Sil Quirin p. 1.*

German Plant Breeders' Right No. PEL 2049, published Aug. 15, 2005, granted Nov. 10, 2006. Copy of certificate attached.

European Plant Breeders' Rights No. 18676 granted Nov. 20, 2006. Copy of certificate and published information from the Community Plant Variety Office site attached.

Canada Plant Breeders' Rights application No. 07–5863 filed Apr. 12, 2007. Copy of published information from Canada Plant Breeders' Right Office web site attached.

Plant material first become available to the public ofn Feb. 20, 2006 as the result of a European sale.

* cited by examiner

*Primary Examiner*—Annette H Para
(74) *Attorney, Agent, or Firm*—Audrey Charles

(57) ABSTRACT

A new and distinct cultivar of *Geranium* plant named 'Sil Quirin', characterized by its semi-double to double type purple-colored flowers, medium green-colored foliage with faint zonation, and vigorous, semi-upright to trailing growth habit.

1 Drawing Sheet

Latin name of genus and species of plant claimed: *Pelargonium peltatum.*
Variety denomination: 'Sil Quirin'.

BACKGROUND OF THE INVENTION

The present invention relates to a new and distinct cultivar of *Geranium* plant botanically known as *Pelargonium peltatum* and hereinafter referred to by the cultivar name 'Sil Quirin'.

The new cultivar originated in a controlled breeding program in Weener, Germany during Summer 2000. The objective of the breeding program was the development of *Pelargonium peltatum* cultivars that are moderately vigorous with unique flower coloration, medium to dark green-colored foliage, trailing growth habit, and low oedema susceptibility.

The new *Geranium* cultivar is the result of cross-pollination. The female (seed) parent of the new cultivar is 'Hillscheider Amethyst', not patented, characterized by its semi-double type violet-colored flowers, medium green-colored foliage with very weak zonation, and moderately, vigorous to vigorous, semi-upright growth habit. The male (pollen) parent of the new cultivar is 'Royal Blue', not patented, characterized by its double type medium to dark purple-colored flowers, medium green-colored foliage without zonation, and vigorous, semi-upright growth habit. The new cultivar was discovered and selected as a single flowering plant within the progeny of the above stated cross-pollination during June 2001 in a controlled environment at Weener, Germany.

Asexual reproduction of the new cultivar by terminal stem cuttings since June 2001 at Weener, Germany and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Sil Quirin' as a new and distinct cultivar of *Geranium* plant:

1. Semi-double to double type, purple-colored flowers;
2. Medium green-colored foliage with faint zonation; and
3. Vigorous, semi-upright to trailing growth habit.

Plants of the new cultivar differ from plants of the female parent primarily in flower color and from plants of the male parent primarily in flower form, leaf shape, and leaf zonation. The leaf margins of the male parent are more palmately lobed than palmatifid.

Of the many commercially available *Geranium* cultivars, the most similar in comparison to the new cultivar is Colorcade Purple 'Balcolpurp', U.S. Plant Pat. No. 13,568. However, in side by side comparisons, plants of the new cultivar differ from plants of 'Balcolpurp' in the following characteristics:

1. Plants of the new cultivar have a different flower color from plants of 'Balcolpurp'; and
2. Plants of the new cultivar have leaf margins that are more deeply indented than plants of 'Balcolpurp'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Sil Quirin'. The plants were grown in 4.5 inch pots for 8 weeks in a greenhouse at West Chicago, Ill. Plants were given one pinch at transplant.

DETAILED BOTANICAL DESCRIPTION

Figure 1:
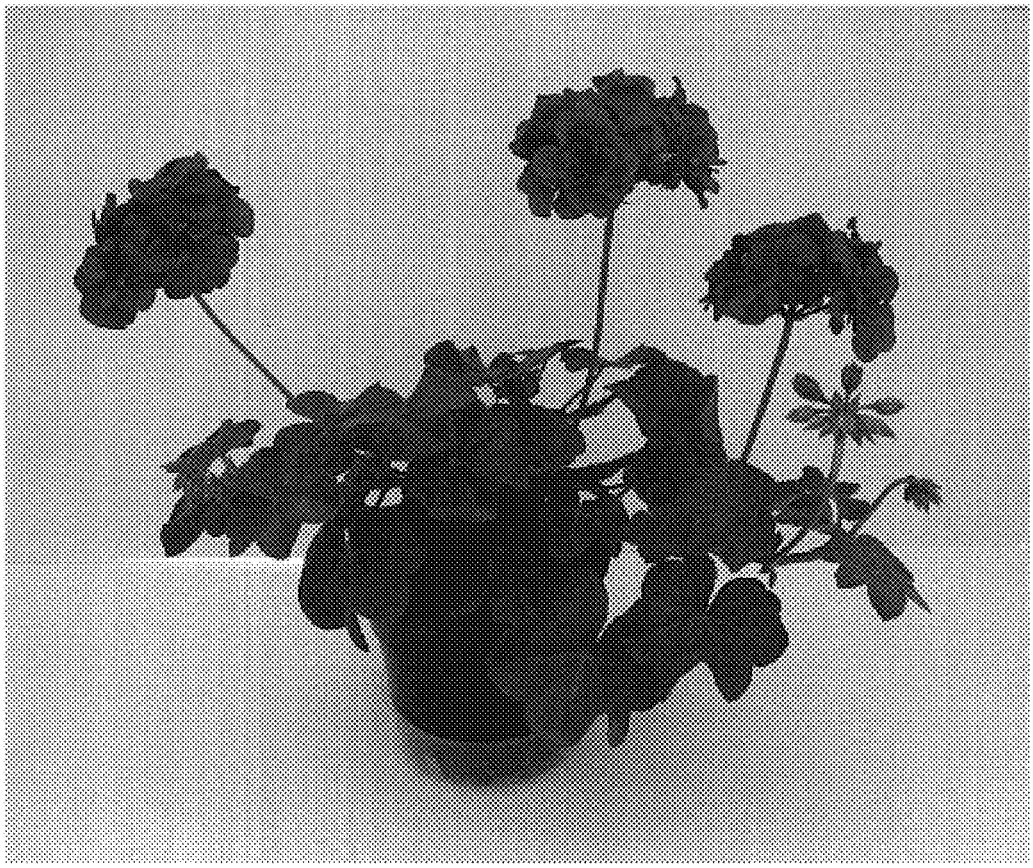
FIG. 1 illustrates a side view of the overall growth and flowering habit of 'Sil Quirin'.
Figure 2:
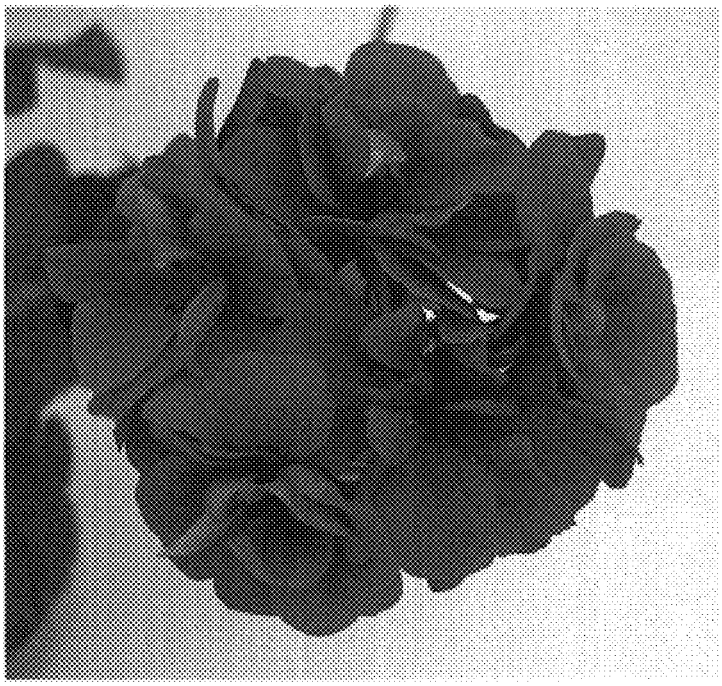
FIG. 2 illustrates a close-up view of an individual umbel of 'Sil Quirin'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 11, 2007 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 8 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Pelargonium peltatum* cultivar Sil Quirin.

Parentage:

*Female parent.*—'Hillscheider Amethyst', not patented.

*Male parent.*—'Royal Blue', not patented.

Propagation:

*Type cutting.*—Terminal stem.

*Time to initiate roots.*—Approximately 11 to 15 days.

*Time to produce a rooted cutting.*—Approximately 28 to 35 days.

*Root description.*—Fibrous.

*Rooting habit.*—Freely branching.

Plant description:

*Commercial crop time.*—Approximately 8 to 10 weeks from a rooted cutting to finish in a 10 cm pot.

*Growth habit and general appearance.*—Vigorous, semi-upright to trailing.

*Size.*—Height from soil level to top of plant plane: Approximately 19.9 cm. Height from soil level to top of foliage: Approximately 12.9 cm. Width: Approximately 27.9 cm.

*Branching habit.*—Freely branching, pinching will increase basal branching. Quantity of main branches per plant: Approximately 3.

*Branch.*—Strength: Strong. Length: Approximately 12.3 cm. Diameter: Approximately 4.0 mm. Length of central internode: Approximately 2.9 cm. Texture: Densely pubescent with a mixture of glandular and nonglandular hairs. Gland color: Colorless, transparent. Color of young stem: 144A. Color of mature stem: 146B.

Foliage description:

*General description.*—Quantity of leaves per lateral branch: Approximately 6. Fragrance: None. Form: Simple. Arrangement: Opposite.

*Leaves.*—Aspect: Petiole is at an acute angle to stem, blade is perpendicular to stem. Shape: Reniform. Margin: Palmatifid. Apex: Rounded. Base: Cordate. Venation pattern: Palmate. Length of mature leaf: Approximately 7.7 cm. Width of mature leaf: Approximately 8.2 cm. Texture of upper surface: Rugous, sparsely pubescent. Texture of lower surface: Rugous, sparsely pubescent on venation. Color of upper surface of young foliage: 137A with zonation of N186A and venation of 144A. Color of lower surface of young and mature foliage: 137C with venation of 144B. Color of upper surface of mature foliage: 137A with faint zonation of N186A and venation of 144A.

*Petiole.*—Length: Approximately 4.7 cm. Diameter: Approximately 2.0 mm. Texture: Pubescent with a mixture of glandular and nonglandular hairs. Gland color: Colorless, transparent. Color: 144A.

Flowering description:

*Flowering habit.*—'Sil Quirin' is freely flowering under outdoor growing conditions with substantially continuous blooming from spring through autumn and year-round in greenhouse environment.

*Lastingness of individual flower on the plant.*—Approximately 10 to 13 days.

Inflorescence description:

*General description.*—Type: Hemispherical umbel. Positioned above foliage. Quantity of fully open umbels per plant: Approximately 2. Quantity of developing umbels per plant: Approximately: 3. Fragrance: None. Length or height: Approximately 4.8 cm. Width: Approximately 7.8 cm. Quantity of fully open flowers per inflorescence: Approximately 9.

*Peduncle.*—Strength: Strong. Aspect: Erect. Length: Approximately 10.2 cm. Diameter: Approximately 3.0 mm. Texture: Sparsely pubescent. Color: 144A.

Flower description:

*General description.*—Type: Semi-double to double.

*Bud.*—Rate of opening: Generally takes 2 to 3 days for bud to progress from first color to fully open flower.

*Bud just before opening.*—Shape: Elliptic. Length: Approximately 1.4 cm. Width: Approximately 9.0 mm. Sepal texture: Densely pubescent with a mixture of glandular and nonglandular hairs. Gland color: Colorless, transparent. Petal texture: Glabrous. Petal color: N74A.

*Corolla.*—Shape: Round. Diameter: Approximately 5.0 cm. Depth: Approximately 2.6 cm.

*Petals.*—Quantity: Approximately 19 petals and 5 irregularly-shaped petaloids per flower. Shape: Obovate. Appearance: Iridescent. Margin: Entire. Apex: Obtuse. Base: Attenuate. Length of upper petals: Approximately 3.2 cm. Width of upper petals: Approximately 2.0 cm. Length of lower petals: Approximately 2.7 cm. Width of lower petals:

Approximately 2.0 cm. Texture of upper and lower surfaces: Glabrous. Color of upper surface of upper petals when fully open: N74A with basal venation of 59A with age petal color transitions to N78A. Color of lower surface of upper petals when fully open: N74B with basal venation of 59B with age petal color transitions to N78B. Color of upper surface of lower petals when fully open: N74A with age transitions to N78A. Color of lower surface of lower petals when fully open: N74B with age transitions to N78B.

*Calyx.*—Shape: 5-pointed star. Diameter: Approximately 2.8 cm.

*Sepals.*—Quantity per flower: Approximately 5. Shape: Lanceolate. Margin: Entire. Apex: Acuminate. Base: Fused. Length of upper sepal: Approximately 1.4 cm. Width of upper sepal: Approximately 5.0 mm. Length of lower sepals: Approximately 1.4 cm. Width of lower sepals: Approximately 3.0 mm. Texture of upper surface: Glabrous. Texture of lower surface: Pubescent with a mixture of glandular and non-glandular hairs. Gland color: Colorless, transparent. Color of upper surface: 144B. Color of lower surface: 144A.

*Pedicel.*—Strength: Strong. Aspect: Acute angle to peduncle. Length: Approximately 2.6 cm. Diameter: Approximately 2.0 mm. Texture: Sparsely pubescent. Color: 144A with 187A where fused to sepals.

*Reproductive organs.*—Androecium: Quantity of mature stamens: Approximately 0 to 3 per flower. Anther shape: Oblong. Anther length: Approximately 3.0 mm. Anther color: N92C. Pollen amount: Moderate. Pollen color: 30C. Gynoecium: Pistil quantity: 1 per flower. Pistil length: Approximately 1.2 cm. Stigma shape: 5 branched. Stigma length: Approximately 3.0 mm. Stigma color: 59A. Style length: Approximately 3.0 mm. Style color: N155D. Ovary length: Approximately 6.0 mm. Ovary texture: Densely pubescent. Ovary color: 143B.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Sil Quirin', substantially as herein shown and described.

* * * * *